United States Patent [19]

Suzuki et al.

[11] 3,939,138

[45] Feb. 17, 1976

[54] RADICAL POLYMERIZATION INITIATOR ANDD PROCESS FOR ITS PREPARATION

[75] Inventors: Souichi Suzuki; Hiroshi Horino, both of Yokohama; Tetsu Ohishi, Tokyo, all of Japan

[73] Assignee: Nippon Zeon Co., Ltd., Tokyo, Japan

[22] Filed: Sept. 4, 1974

[21] Appl. No.: 503,189

[30] Foreign Application Priority Data

Sept. 6, 1973 Japan................................ 48-99675

[52] U.S. Cl. ................ 260/100; 252/415; 260/97.5
[51] Int. Cl.² .............................................. C09F 1/40
[58] Field of Search ............ 260/100, 97.5; 252/415

[56] References Cited
UNITED STATES PATENTS

| | | | |
|---|---|---|---|
| 3,223,696 | 12/1965 | Boylan | 260/100 |
| 3,518,214 | 6/1970 | Wheelus | 260/97.5 |
| 3,567,704 | 3/1971 | Schuller | 260/97.5 |

*Primary Examiner*—M. J. Welsh
*Assistant Examiner*—William E Parker
*Attorney, Agent, or Firm*—Sherman & Shalloway

[57] ABSTRACT

A radical polymerization initiator comprising as an active ingredient a hydroperoxide of disproportionated or hydrogenated rosin acid or its alkali metal or ammonium salt.

The initiator is prepared by contacting disproportionated or hydrogenated rosin acid or its alkali metal or ammonium salt with molecular oxygen in water or an organic solvent at a temperature of 0° to 150°C. to form its hydroperoxide.

9 Claims, No Drawings

RADICAL POLYMERIZATION INITIATOR AND PROCESS FOR ITS PREPARATION

This invention relates to a radical polymerization initiator having a hydrophilic group and being suitable for low temperature polymerization, and to a process for its preparation.

In the radical-initiated solution- or emulsion-polymerization of a vinyl monomer in an aqueous medium, the use of a hydrophilic radical polymerization initiator is advantageous because it leads to the stabilization of the reaction system and the uniform proceeding of the polymerization. For low temperature (for example, lower than 10°C.) polymerizations, only redox-type catalysts have previously been known as radical polymerization initiators, and no polymerization initiator containing a hydrophilic group has ever been known.

Accordingly, it is an object of this invention to provide a novel radical polymerization initiator which is suitable for low temperature polymerizations and exhibits hydrophilic properties.

We have found that a product obtained by disproportionating or hydrogenating rosin acid, which is readily available in nature, and then hydroperoxidizing the resulting product, has a carboxyl group as a hydrophilic group, and suits the above object of this invention.

According to this invention, there are provided a radical polymerization initiator containing as an effective ingredient a hydroperoxide of disproportionated or hydrogenated rosin acid or its alkali metal or ammonium salt, and a process for preparing the radical polymerization initiator which comprises contacting disproportionated or hydrogenated rosin acid or its alkali metal or ammonium salt in water or an organic solvent with molecular oxygen at a temperature of 0° to 150°C. to form its hydroperoxide.

It has been known that rosin acid spontaneously oxidizes to form its oxide and peroxide. However, these oxidation products are not effective as radical polymerization initiators, but rather inhibit polymerizations. It is unexpected therefore that an oxidation product of disproportionated or hydrogenated rosin acid acts as a superior radical polymerization initiator.

The radical polymerization initiator of this invention has a hydrophilic group. Because of this, the radical initiator of this invention generates radicals on interfaces of monomer particles or polymer particles containing monomers or aqueous solutions. The generated radical, either directly or after reaction with the monomer nearby to form oligomer radicals, enters the insides of the particles and is oriented, whereas the hydrophilic group remains on the surfaces of the particles. Thus, when the hydroperoxide in accordance with this invention is used, the emulsifier adds to the end of the polymer obtained and is oriented in the aqueous phase. Accordingly, the hydrophilic group can be distributed on the interfaces of the particles with better efficiency than in the case of copolymerizing a water-soluble monomer. It is a further feature of this invention that the stability of the latex is superior because of this hydrophilic group.

The radical polymerization initiator of this invention can also act as an emulsifier. The initiator of this invention has a good balance between hydrophilicity and oleophilicity, and is oriented on the interfaces of polymer particles, interfaces of monomer particles, and in the case of emulsion polymerization, also micelle interfaces in which case the initiator itself contributes as an emulsifier to the stability of the emulsion. When the radical polymerization initiator of this invention is used as a redox initiator in a low temperature polymerization together with a reducing agent, it is more liable to generate radicals since the reducing agent is generally water-soluble and the peroxide readily makes contact with the reducing agent at the interface between the monomer and water. Since the generated radicals are present near the monomer, the efficiency of the initiator is high. Accordingly, in this case, the radical polymerization initiator of this invention is an ideal initiating system.

The radical polymerization initiator of this invention is furthermore active at low temperatures. It may be used alone or together with a reducible metal salt to form a redox system. In either case, it easily initiates polymerizations. The rate of polymerization can be freely controlled according to the amount of the radical initiator of this invention used. In a polymerization initiation system at low temperatures, the rate of polymerization is not so much affected only by changing the amount of the conventional peroxide and considerable difficulties are encountered in obtaining the desired rate of polymerization. In contrast, the rate of polymerization can be controlled with good reproducibility by varying the amount of the radical polymerization initiator of this invention. Furthermore, the radical polymerization initiator of this invention has a great ability to complete the polymerization. Since the conventional water-soluble polymerization initiators, especially hydrogen peroxide or a persulfate, have strong hydrophilicity, the rate of polymerization is markedly reduced towards the end of the polymerization reaction when the concentration of the monomer becomes low. In contrast, the initiator of this invention can give rise to a polymerization conversion of at least 95% without hardly any reduction in the rate of polymerization.

As stated above, the hydroperoxide initiator of this invention acts both as an emulsifier and a polymerization initiator, and these activities together with its function after adding to the polymer on decomposition are also superior.

The hydroperoxide of rosin acid or its alkali metal or ammonium salt in this invention can be prepared by disproportionating or hydrogenating natural rosin, and then hydroperoxidizing or hydroperoxidizing and saponifying the resultant product. The saponification may be performed before hydroperoxidization. The starting natural rosin includes, for example, gum rosin, wood rosin, or tall oil rosin, and is composed mainly of abietic acid, levopimaric acid, palustric acid, dehydroabietic acid, tetrahydroabietic acid and neoabietic acid. The hydroperoxide is obtained as a mixture of the starting material and its intermediate (content 20–35%). But when used as a polymerization initiator, it need not be purified in particular, but can be in the form of the mixture.

The process for preparing the polymerization initiator of this invention will be described specifically.

First, disproportionated or hydrogenated rosin acid or its alkali metal or ammonium salt (to be abbreviated below as rosin) is oxidized with molecular oxygen in water or an organic solvent inert to oxygen to form a hydroperoxide. Oxygen and air are, for example, used as the molecular oxygen. The concentration of the rosin in the solvent is not particularly limited. However, if the concentration is too high, the salt is apt to precipitate, and when it is too low, the efficiency is poor. Accordingly, the suitable concentration of the rosin is 10 to 30% by weight. As the reaction temperature is increased, the rate of absorption of oxygen increases, but the rate of the decomposition of the resulting peroxide also increases. If the temperature is too high, the yield of the peroxide is poor. At low temperatures, the reduction in yield caused by the decomposition of the peroxide can be prevented, but the rate of absorption of oxygen is slow, and long periods of time are required for the reaction. The reaction temperature that can be employed is 0° to 150°C., preferably 20° to 100°C.

The reaction can take place fully without the aid of an initiator, but when no initiator is used, the induction period becomes longer and indefinite. In order to shorten the induction period and promote the reaction, it is preferred to use an initiator conjointly. Examples of the initiator are azo compounds, alkyl peroxides, acyl peroxides, hydroperoxides, ketone peroxides, per esters, peroxy carbonates, persulfates, and hydrogen peroxide. The use of a radical reaction initiator is effective, and ultraviolet rays can also be used. Conveniently, the reaction can be performed while adding a part of the rosin peroxide prepared in the previous reaction. In order to shorten the induction period of the reaction, it is also effective to initiate the reaction at a temperature about 20° to 30°C. higher than the prescribed reaction temperature, and to lower the temperature to the desired point when the absorption of oxygen begins. The pressure of oxygen or air can be either normal atmospheric pressure or elevated pressures (usually 0 to 100 Kg/cm².G). In order to promote the reaction, it is desirable to elevate the pressure to some degree. Furthermore, in order to ensure good contact between gas and liquid, it is desirable to blow oxygen into the reaction mixture or to stir the reaction mixture sufficiently.

The hydroperoxide of this invention cannot be obtained if rosin acid, neither disproportionated nor hydrogenated, is used. The hydroperoxide of the salt of rosin acid can be either one obtained by hydroperoxiding rosin acid and then saponifying the product, or one obtained by hydroperoxidizing a rosin acid salt. Generally, the latter is advantageous from the production viewpoint.

The polymers are prepared in an aqueous media using the radical polymerization initiator of this invention utilizing emulsion-, suspension-, and aqueous-polymerization techniques. The amount of the initiator used is 0.01 to 10 parts by weight per 100 parts by weight of the monomer.

In the case of emulsion-polymerization, a monomer is emulsified and dispersed with stirring in an aqueous solution of the radical polymerization initiator in a reactor free from oxygen, and then polymerized at a temperature of not more than 100°C., preferably 0° to 80°C. The pH of the polymerization system is not particularly restricted, but preferably the polymerization is carried out at a pH of at least 8. If desired, an anionic, cationic, nonionic or amphoteric emulsifier, a dispersant, an emulsification assistant such as inorganic salts, and a molecular weight adjuster for example, a sulfur compound such as tertiary dodecyl mercaptan or diisopropyl dixanthogen disulfide, or a halogen compound such as carbon tetrachloride or carbon tetrabromide can be used.

In the case of suspension polymerization, the radical polymerization initiator is formed into an aqueous solution having a concentration lower than the critical micelle concentration in a reactor free from oxygen, and a suspension is formed while stirring the monomer; and the polymerization of the monomer is carried out at a temperature of not more than 100°C., preferably 0 to 90°C. If desired, there can be used a stabilizer, for example, natural polymers or their derivatives such as gelatin, tragacanth, starch, methyl cellulose, or carboxymethyl cellulose; water-soluble polymers such as polyvinyl alcohol, partially saponified polyvinyl alcohol, vinyl alcohol copolymers, or polyacrylic acid; difficulty soluble salts such as $BaSO_4$, $CaSO_4$, $BaCO_3$, $CaCO_3$, $MgCO_3$ or $Ca_3(PO_4)_2$; inorganic polymers such as talc, bentonite, silicic acid, diatomaceous earth or clay; and difficulty soluble finely divided inorganic compounds such as metal or metal oxide powders, or a stabilization assistant such as NaCl, KCl or $Na_2SO_4$ or other salts.

In the case of aqueous solution-polymerization, a water-soluble monomer is added to an aqueous solution of this polymerization initiator of this invention in a reaction vessel free from oxygen, and the monomer is polymerized at a temperature of not more than 100°C., preferably 0° to 80°C.

In these polymerizations, conventional polymerization initiators can also be used conjointly.

The mechanism of polymerization using the radical polymerization initiator of this invention will be described below with reference to emulsion polymerization as an example.

When the concentrations of water, the monomer and the radical polymerization initiator exceed the critical micelle concentration in the polymerization system, micelles are formed. When the monomer is dispersed in this aqueous solution, a very small amount of the monomer is solubilized in the micelle, and a greater part of the monomer becomes liquid droplets protected by the radical polymerization initiator. If the system is properly stirred, it separates into an aqueous phase, a micelle phase and a phase of the liquid droplets of the monomer. The polymerization of the monomer begins by heating the system to a predetermined temperature or adding a promotor to form a redox catalyst system in order to obtain radicals from the polymerization initiator. Radicals are generated at the interface between the micelle phase and the monomer liquid phase. The generated radicals either directly or after reaction with the monomer nearby to form oligomer radicals, enter the droplets of the monomer or the micelle to initiate the polymerization of the monomer solubilized, and to form polymer particles. At this time, the hydrophilic group of the generated radicals is distributed with good efficiency on the interfaces of the particles. Accordingly, the unreacted radical polymerization initiator contributes to the stability of the emulsion as an emulsifier, and the fragments of the initiator attached to the ends of the polymer contributes to the stability of the latex.

Monomers that can be polymerized using the radical polymerization initiator of this invention are any radical-polymerizable monomers. For example, there can be used diene monomers such as 1,3-butadiene, isoprene, 2,3-dimethyl-1,3-butadiene, 2-ethyl-1,3-butadiene, 1,3-pentadiene or chloroprene, unsaturated nitriles such as acrylonitrile, methacrylonitrile, α-chloroacrylonitrile, or α-cyanoethyl acrylonitrile; monovinylidene aromatic hydrocarbons such as styrene, an alkyl styrene (e.g., o-, m- or p-methyl styrene or ethyl styrene), vinyl naphthalene or halogenated monovinylidene aromatic hydrocarbons (e.g., o-, m- or p-chlorostyrene, or 2,4-dibromostyrene); unsaturated carboxylic acids or the esters thereof such as acrylic acid, methacrylic acid, crotonic acid, itaconic acid, maleic acid, fumaric acid, methyl acrylate, butyl acrylate, 2-ethylhexyl acrylate or methyl methacrylate; vinyl esters such as vinyl pyridine or vinyl acetate; and vinylidene halides such as vinylidene chloride or vinylidene bromide. These monomers can be used either alone or in admixture of two or more.

The following Examples illustrate the present invention in greater detail.

EXAMPLE 1

A 0.5 liter autoclave was charged with 200 g of an aqueous solution of disproportionated potassium rosinate (solids content 23%, pH = 10.6; to be abbreviated as rosin soap). After sealing the autoclave, oxygen was introduced into the autoclave to a pressure of 15 Kg/cm$^2$.G, and while being maintained at 40°C., the aqueous solution was stirred by an electromagnetic induction stirrer. In about 23 hours, the absorption of oxygen began, and in 46 hours, a pressure reduction amounting to 4.9 Kg/cm$^2$ was observed.

The contents were withdrawn, and the peroxide was determined using potassium iodide. The concentration of the peroxide was found to be 0.16 mol/liter. The conversion of the rosin soap to the peroxide corresponded to 23.6 mol%.

EXAMPLE 2

A 1-liter autoclave was charged with 475 g of the same rosin soap solution as used in Example 1 and 25 g of the aqueous solution of peroxidized rosin soap prepared in Example 1, and reacted at an initial oxygen pressure of 30 Kg/cm$^2$.G and at a temperature of 60°C. for 23 hours. The reduction of the oxygen pressure was 11.6 Kg/cm$^2$, and the conversion of the rosin soap to the peroxide was 31.0 mol%.

EXAMPLE 3

Same as Example 2, except that the reaction temperature in the initial stage was changed to 80°C., and lowered to 60°C. when the absorption of oxygen began. Then, the reaction was performed at this temperature. After 20.5 hours, there was a reduction in oxygen pressure which amounted to 10.7 Kg/cm$^2$ in total. Titration showed that the conversion of the rosin soap to the peroxide was 28.5 mol%.

The above procedure was repeated except that potassium rosinate not disproportionated was used. The pressure after 20 hours was 5 Kg/cm$^2$, and the conversion was 1 mol%.

EXAMPLES 4 to 7

Polymerization was carried out in accordance with Polymerization Recipe 1 shown in Table 1 using the disproportionated potassium rosinate hydroperoxide prepared in Example 3. Except the low boiling monomer and the promotor, all of the ingredients in the polymerization recipe were placed in a glass bottle having a capacity of about 1 liter. Dissolved oxygen was removed by repeating the pressure reduction and the nitrogen purging. Then, the remaining monomer was fed into the glass bottle. The autoclave was plugged and sealed, and rotated in the longitudinal direction in a constant temperature vessel at 5°C. Then, the promotor was fed from the plug to initiate the polymerization. The results are shown in Table 1.

Table 1

| Polymerization Recipe 1 Starting materials | Amounts blended (parts by weight) |
|---|---|
| Butadiene | 66 |
| Acrylonitrile | 34 |
| Water | 200 |
| Emulsifier (potassium rosinate) | See Table 2 |
| Water-soluble polymerization initiator | See Table 2 |
| Sodium carbonate | 0.1 |
| Tertiary dodecyl mercaptan | 0.4 |
| Ferrous sulfate | 0.01 |
| Trisodium ethylenediaminetetraacetate | 0.03 |
| Sodium formaldehyde sulfoxylate | 0.2 |

Table 2

| | Contrast | | | | Example | | | |
|---|---|---|---|---|---|---|---|---|
| | 1 | 2 | 3 | 4 | 4 | 5 | 6 | 7 |
| Water-soluble polymerization initiator (parts by weight) | | | | | | | | |
| Succinic acid hydroperoxide | 0.2 | — | — | — | — | — | — | — |
| Hydrogen peroxide | — | 0.2 | — | — | — | — | — | — |
| Potassium persulfate | — | — | 0.2 | — | — | — | — | — |
| Ammonium persulfate | — | — | — | 0.2 | — | — | — | — |
| Potassium rosinate hydroperoxide (amount of the pure product) | — | — | — | — | 0.05 | 0.1 | 0.2 | 0.3 |
| Emulsifier (parts by weight) | | | | | | | | |
| Potassium rosinate | 2.3 | 2.3 | 2.3 | 2.3 | 2.45 | 2.4 | 2.3 | 2.2 |
| Polymerization Conversion (%) | | | | | | | | |
| 4 hours after initiation of polymerization | 1 | 2 | 7 | 6 | 15 | 21 | 29 | 38 |
| 8 hours after initiation of polymerization | 2 | 2 | 17 | 16 | 33 | 41 | 60 | 85 |
| 16 hours after initiation of polymerization | 5 | 2 | 46 | 44 | 66 | 84 | 98 | 99 |

For comparison, the rate of polymerization was examined when succinic acid hydroperoxide, hydrogen peroxide, potassium persulfate or ammonium persulfate as a water-soluble polymerization initiator was used in the production of acrylonitrile/butadiene rubber. The amount of the peroxide used was 0.2 phm. It was found that the rate of polymerization was slower than in the case of using potassium rosinate hydroperoxide used in Example 6.

In Examples 4 to 7, the total amount of the emulsifier and peroxide was maintained constant, and the amount of the peroxide was varied. It was found that the rate of polymerization varied greatly with the amount of the peroxide when the potassium rosinate hydroperoxide was used. From this, it is clear that the rate of polymerization can be controlled according to the amount of the peroxide. From the fact that in Examples 6 and 7, the polymerization conversion was 98 and 99%, respectively, when the reaction time was 16 hours, it is clear that the potassium rosinate hydroperoxide had the ability to perform complete polymerization.

EXAMPLES 8 to 13

In order to show that rosin acid hydroperoxide is a universal radical initiator, typical radical-polymerizable monomers were polymerized using it. The polymerization procedure was the same as that used in Example 4. The results are shown in Table 3.

Table 3

|  | Examples | | | | | |
| --- | --- | --- | --- | --- | --- | --- |
|  | 8 | 9 | 10 | 11 | 12 | 13 |
| Monomers (parts by weight) | | | | | | |
| Styrene | 100 | — | — | — | — | — |
| Acrylonitrile | — | 100 | — | — | — | — |
| Methyl methacrylate | — | — | 100 | — | — | — |
| Methacrylic acid | — | — | — | 100 | — | — |
| Butadiene | — | — | — | — | 100 | — |
| Isoprene | — | — | — | — | — | 100 |
| Polymerization conversion (%) after the prescribed periods of time | | | | | | |
| 4 hours | 70 | 65 | 95 | 91 | 5 | 5 |
| 8 hours | 99 | 96 | 100 | 98 | 10 | 12 |
| 16 hours | 99 | 99 | 100 | 98 | 15 | 18 |

It is seen from Table 3 that potassium rosinate hydroperoxide can be used as an initiator in the polymerization of any of styrene, acrylonitrile, methyl methacrylate, methacrylic acid, butadiene and isoprene which are typical radical-polymerizable monomers, and there can be attained a rate of polymerization proportional to the polymerization rate constant inherent to each of the monomers.

EXAMPLES 14 to 16

These Examples show that disproportionated rosin hydroperoxide is effective as a thermally decomposable polymerization initiator. Acrylonitrile and butadiene were copolymerized in accordance with the procedure of Example 4 using the emulsion polymerization recipe 2 shown in Table 4 at a temperature of 40°C. The results are shown in Table 4.

Table 4

|  | Example 14 | Example 15 | Example 16 |
| --- | --- | --- | --- |
| Polymerization recipe 2 (parts by weight) | | | |
| Butadiene | 66 | 66 | 66 |
| Acrylonitrile | 34 | 34 | 34 |
| Water | 200 | 200 | 200 |
| Potassium oleate | 2.05 | 1.6 | — |
| Sodium naphthalene-sulfonate/ formaldehyde condensate | 0.2 | 0.2 | — |
| Potassium rosinate hydroperoxide | 0.01 | 0.1 | 0.8 |
| Potassium rosinate | 0.04 | 0.4 | 3.2 |
| Sodium carbonate | 0.1 | 0.1 | 0.1 |
| Tertiary decyl mercaptan | 0.4 | 0.4 | 0.4 |
| Polymerization conversions (%) after the prescribed periods of time | | | |
| 4 hours | 20 | 21 | 22 |
| 8 hours | 44 | 50 | 72 |
| 16 hours | 81 | 90 | 100 |

In these Examples, the amount of the peroxide was varied to 0.01, 0.1, and 0.8 phm. Consequently, it was found that the rate of polymerization is higher as the amount of the peroxide is larger. However, as is seen from Example 14, a sufficiently feasible rate of polymerization was attained when the amount of the peroxide was as small as 0.01 phm. This shows that potassium rosinate hydroperoxide can be used as a thermally decomposable peroxide.

EXAMPLE 17

In this Example, the efficiency of the peroxide as an initiator was examined. Acrylonitrile and butadiene were polymerized in emulsion in accordance with the same polymerization recipe as Example 6 using diisopropyl benzene hydroperoxide (DiP) (comparison), and potassium rosinate hydroperoxide (RKHP) (invention) while adjusting the pH of the polymerization system to 10.3. The rate of polymerization was measured.

The peroxide was dissolved in a 2% aqueous solution of rosin soap of pH 10.3, and ferrous sulfate was used as a reducing agent at 5°C. Then, the rate of decomposition of the peroxide was measured.

The results are shown in Table 5 below.

Table 5

|  | Comparison | Example 17 |
| --- | --- | --- |
| Perodixe | DiP | RKHP |
| Rate of decomposition | $6 \times 10^2$ l/mol.hr. | $1 \times 10^2$ l/mol.hr. |
| Rate of polymerization | 7%/hr | 8%/hr |

The reaction between the peroxide (ROOH) and $Fe^{++}$ salt is expressed by equation (1), and the decomposition rate constant ($ki$) at a given pH is expressed by equation (2).

$$ROH + Fe^{++} \xrightarrow{ki} RO \cdot + {}^-OH + Fe^{+++} \quad (1)$$

$$ki = \frac{\ln[ROOH]_o/[ROOH]}{[Fe^{++}] \cdot t} \quad (2)$$

$[ROOH]_o$ ... the initial concentration of the peroxide $t$ ... the reaction time

[ROOH] ... the concentration of the peroxide at a given reaction time $t$

[$Fe^{++}$] ... the concentration of $Fe^{++}$ at a given reaction time $t$

The rate of decomposition was determined in accordance with equation (2) after measuring [ROOH]$_0$, [ROOH] and $t$. [$Fe^{++}$] was not actually measured, but was calculated on the basis of the concentration of $Fe^{++}$ salt as charged. The rate of reaction between DiP and $Fe^{++}$ salt was calculated as 1330 l/mol.hr. according to the literature (Can. Journal Chem. 30, 985, 1952), which value does not correspond with that given in Table 5. This is presumably because the concentration of $Fe^{++}$ salt was not actually measured, but was calculated on the basis of the concentration of $Fe^{++}$ salt as charged in order to know the relative decomposition rates between DiP and RKHP; the pH was different; and the decomposition was performed in the aqueous soap solution.

The efficiency of the initiator cannot be evaluated directly from the rate of decomposition and the rate of polymerization. When the efficiency of the initiator is examined in regard to the rate of polymerization, the rate of polymerization of DiP is lower than that of RKHP in spite of the fact that the rate of decomposition of DiP is far greater than that of RKHP. From this, it can be seen that RKHP is a peroxide having good efficiency in regard to the rate of polymerization.

EXAMPLE 18

Using disproportionated potassium rosinate hydroperoxide prepared in Example 2, polymerization was performed in accordance with the polymerization recipe shown in Table 6. The mechanical stability of the resultant latex was measured. The results are shown in Table 6.

Table 6

|  | Comparison 1 | Comparison 2 | Example 18 |
| --- | --- | --- | --- |
| Polymerization recipe (parts by weight) | | | |
| Butadiene | 66 | 66 | 66 |
| Acrylonitrile | 34 | 34 | 34 |
| Distilled water | 210 | 210 | 210 |
| Potassium rosinate | 2.65 | 2.3 | 2.1 |
| Potassium rosinate hydroperoxide | — | — | 0.2 |
| Sodium carbonate | 0.1 | 0.1 | 0.1 |
| Tertiary dodecyl mercaptan | 0.4 | 0.4 | 0.4 |
| Ferrous sulfate | 0.004 | 0.005 | 0.01 |
| Trisodium ethylenediamine tetraacetate | 0.02 | 0.02 | 0.02 |
| Sodium formaldehyde sulfoxylate | 0.2 | 0.2 | 0.2 |
| Diisopropyl benzene hydroperoxide | 0.2 | 0.2 | — |
| Polymerization temperature (°C.) | 5 | 5 | 5 |
| Initial rate of polymerization (%/hr) | 10 | 10 | 10 |
| Final polymerization conversion (%) | 89.5 | 90.5 | 90.0 |
| Amount of the coagulated substance at the time of polymerization (%) | 0.2 | 0.5 | 0.2 |
| Mechanical stability of the latex (%) | 1 | 4 | 1 |

The mechanical stability of the latex was tested by the Hamilton Beach mixer method [H. F. Jordan. P. D. Brass, C. P. Roe: Ind. Eng. Chem., 9, 182 (1937)]. Specifically, 250 g of a sample latex was placed in a receptacle, and its temperature was adjusted to 50° ± 1°C. Then, the spindle was rotated for 5 minutes at a speed of 15000 rpm, and the amount (%) of the resulting coagulated substance was measured.

The mechanical stability of the latex is affected by such factors as the particle diameter of the latex or its soap coverage. Accordingly, in this Example and the experiments of Comparisons 1 and 2, the rate of polymerization was maintained at the same level according to the amounts of the iron ion and the peroxide. It can be seen from Table 6 that when rosin soap hydroperoxide was used, the amount of the coagulated substance formed in the polymerization was small, and the latex had good mechanical stability.

EXAMPLE 19

Oxidation reaction was performed in the same way as in Example 3 using hydrogenated potassium rosinate (Staybelite Resin, a product of Hercules Incorporated). After performing the reaction for 18 hours, there was a reduction in oxygen pressure amounting to 14.6 Kg/cm² in total. Titration showed that the conversion of the hydrogenated potassium rosinate to a peroxide was 33.9 mol%.

Acrylonitrile and butadiene were copolymerized using 0.1 part by weight, calculated as the amount of the pure product per 100 parts by weight of the monomers, of the resulting peroxide. The polymerization conversion was 27% after 4 hours from the initiation of polymerization, 55% after 8 hours, and 98% after 16 hours. There was obtained a rubber latex having superior mechanical stability.

What we claim is:

1. A radical emulsion-, suspension-, or aqueous-polymerization initiator consisting essentially of as an active ingredient a hydroperoxide of disproportionated rosin acid, alkali metal salt thereof, ammonium salt thereof, hydrogenated rosin acid, alkali metal salt thereof, or ammonium salt thereof, said active ingredient being prepared by contacting disproportionated rosin acid, alkali metal salt thereof, ammonium salt thereof, hydrogenated rosin acid, alkali metal salt thereof, or ammonium salt thereof with molecular oxygen in water or an organic solvent in the presence of a radical reaction initiator at a temperature of 0° to 150°C. and a pressure of 0 to 100 kg/cm².G to form the hydroperoxide thereof.

2. The radical polymerization initiator of claim 1 wherein said active ingredient is a hydroperoxide of disproportionated potassium rosinate, said active ingredient being prepared by contacting disproportionated potassium rosinate with molecular oxygen in water or in an organic solvent in the presence of a radical reaction initiator at a temperature of 5° to 150°C. and a pressure of 0 to 100 Kg/cm².G to form its hydroperoxide.

3. A process for preparing a radical emulsion-, suspension-, or aqueous-polymerization initiator consisting essentially of, as an active ingredient, a hydroperoxide of a member selected from the group consisting of disproportionated rosin acid, alkali metal salt thereof, ammonium salt thereof, hydrogenated rosin acid, alkali metal salt thereof, and ammonium salt thereof, which process comprises contacting said member with molecular oxygen in water or an organic solvent in the presence of a radical reaction initiator at a temperature of 5° to 150°C. and a pressure of 0 to 100 Kg/cm².G to form the hydroperoxide thereof.

4. The process of claim 3 wherein the active ingredient is the hydroperoxide of disproportionated potassium rosinate obtained by contacting disproportionated potassium rosinate with molecular oxygen in water or in an organic solvent in the presence of a radical initiator at a temperature of 5° to 150°C. and a pressure of 0 to 150 Kg/cm².G 5. The process of claim 3 wherein the reaction temperature is from 20° to 100°C.

6. The process of claim 5 wherein the reaction temperature is from 40° to 60°C. and the pressure is from 10 to 30 kg/cm².G.

7. In a radical emulsion-polymerization process, the improvement comprising using the radical emulsion-polymerization initiator of claim 1.

8. In a radical suspension-polymerization process, the improvement comprising using the radical suspension-polymerization initiator of claim 1.

9. In a radical aqueous-polymerization process, the improvement comprising using the radical aqueous-polymerization initiator of claim 1.

* * * * *